(12) United States Patent
Tenne et al.

(10) Patent No.: US 8,182,523 B2
(45) Date of Patent: May 22, 2012

(54) STENT DELIVERY SYSTEM WITH IMPROVED RETRACTION MEMBER

(75) Inventors: Dirk Tenne, Miami Beach, FL (US); Vladimir Mitelberg, Aventura, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 302 days.

(21) Appl. No.: 12/694,709

(22) Filed: Jan. 27, 2010

(65) Prior Publication Data
US 2010/0137968 A1   Jun. 3, 2010

Related U.S. Application Data

(62) Division of application No. 11/380,819, filed on Apr. 28, 2006, now Pat. No. 7,655,031.

(51) Int. Cl.
*A61F 2/06* (2006.01)
(52) U.S. Cl. ...................................... 623/1.11
(58) Field of Classification Search ........ 623/1.11–1.23; 606/108, 191–198
See application file for complete search history.

(56) References Cited

U.S. PATENT DOCUMENTS

| | | | |
|---|---|---|---|
| 5,288,711 A | 2/1994 | Mitchell et al. | |
| 5,516,781 A | 5/1996 | Morris et al. | |
| 5,563,146 A | 10/1996 | Morris et al. | |
| 5,646,160 A | 7/1997 | Morris et al. | |
| 6,027,510 A | 2/2000 | Alt | |
| 6,258,099 B1 | 7/2001 | Mareiro et al. | |
| 6,569,192 B1 | 5/2003 | Foreman et al. | |
| 6,582,460 B1 * | 6/2003 | Cryer ........................... | 623/1.11 |
| 6,673,106 B2 | 1/2004 | Mitelberg et al. | |
| 6,818,013 B2 | 11/2004 | Mitelberg et al. | |
| 6,833,003 B2 | 12/2004 | Jones et al. | |
| 6,955,685 B2 | 10/2005 | Escamilla et al. | |
| 6,960,227 B2 | 11/2005 | Jones et al. | |
| 7,309,351 B2 * | 12/2007 | Escamilla et al. ........... | 623/1.12 |
| 2002/0082683 A1 | 6/2002 | Stinson et al. | |
| 2002/0099432 A1 * | 7/2002 | Yee .............................. | 623/1.11 |
| 2004/0059407 A1 | 3/2004 | Escamilla et al. | |
| 2004/0102832 A1 | 5/2004 | Doty | |
| 2005/0038496 A1 | 2/2005 | Jones et al. | |
| 2005/0049668 A1 | 3/2005 | Jones et al. | |
| 2005/0049669 A1 | 3/2005 | Jones et al. | |
| 2005/0049670 A1 | 3/2005 | Jones et al. | |
| 2006/0025845 A1 | 2/2006 | Escamilla et al. | |

* cited by examiner

*Primary Examiner* — Kevin T Truong
(74) *Attorney, Agent, or Firm* — Cook Alex Ltd.

(57) ABSTRACT

An expandable stent and delivery system is provided for treating body vessel defects, such as partially occluded blood vessels and aneurysms. The delivery system includes a core member having a non-cylindrical retraction member with extending portions configured to extend between struts of the stent. The stent includes enlarged anchor members that cooperate with the retraction member to secure the stent to the core member for movement within a delivery catheter and deployment to a body vessel defect. The extending portions provide a greater contact area than would be possible with a cylindrical retraction member, which is especially beneficial when retracting a partially deployed stent into the catheter.

8 Claims, 3 Drawing Sheets

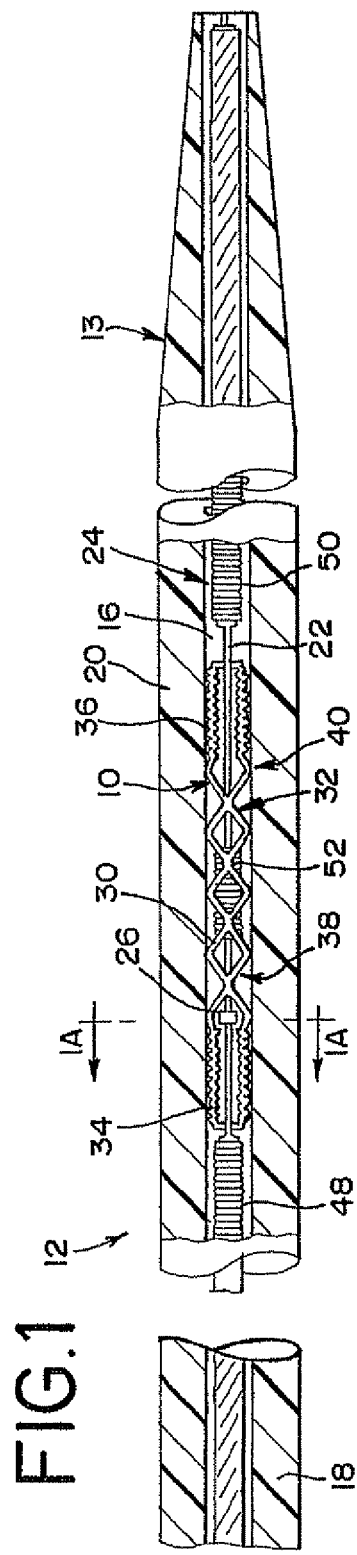
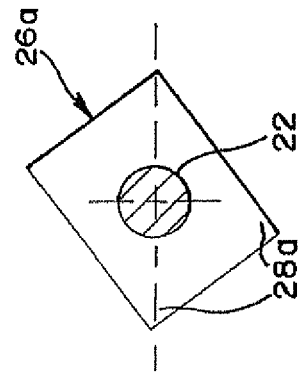
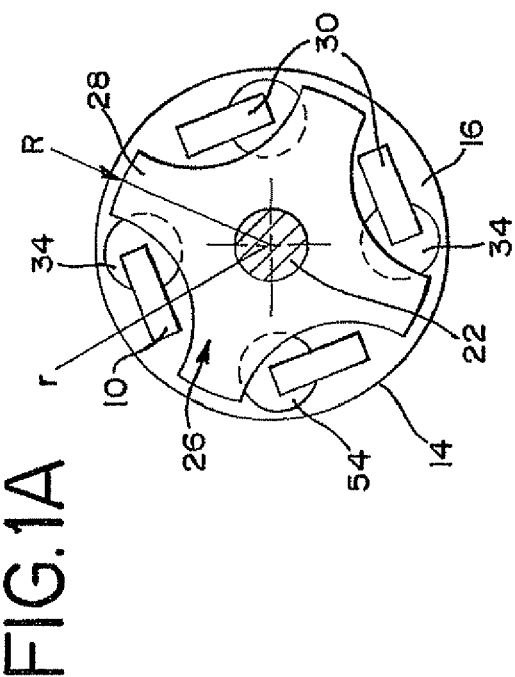

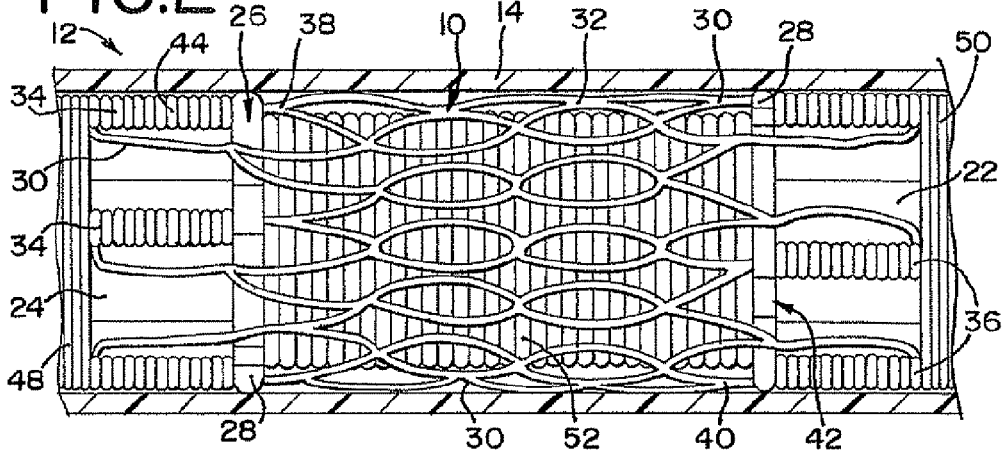
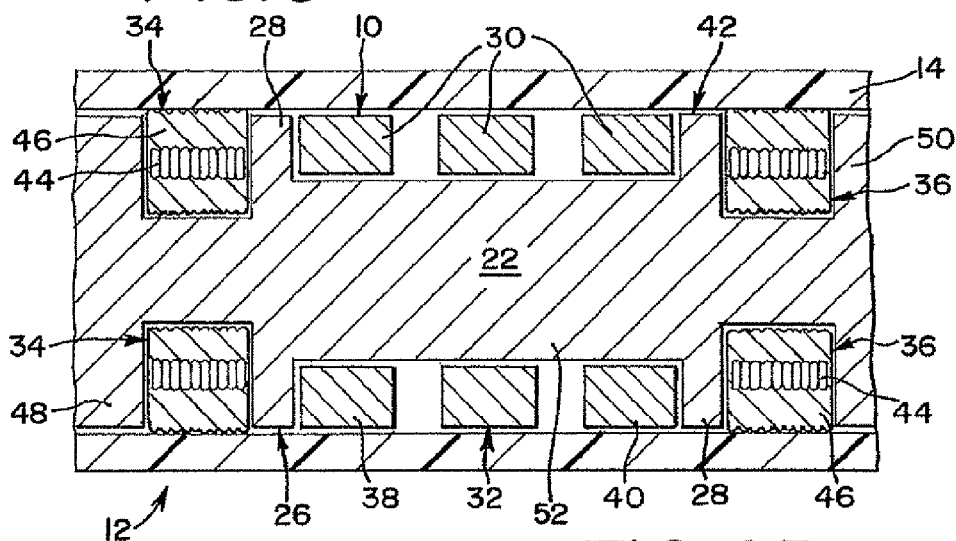
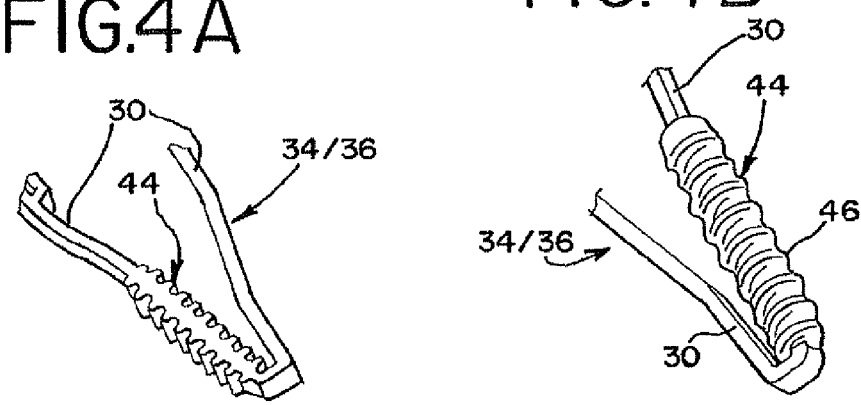

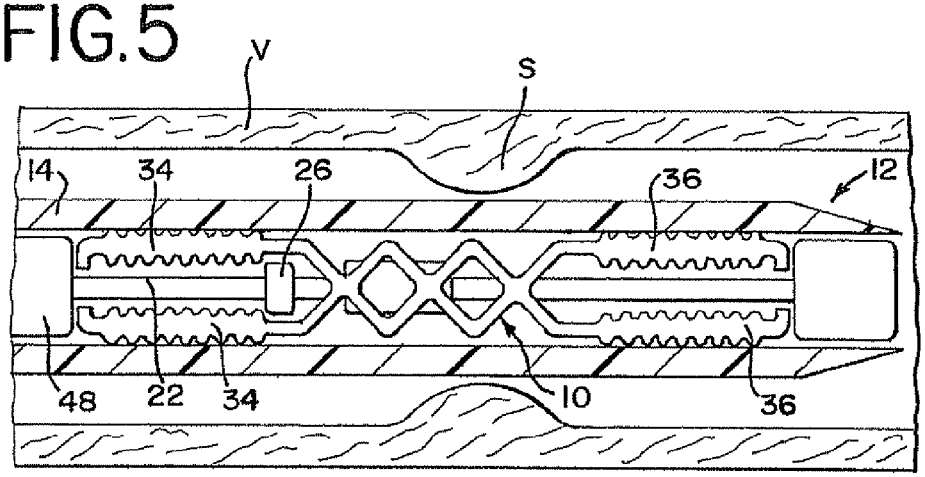
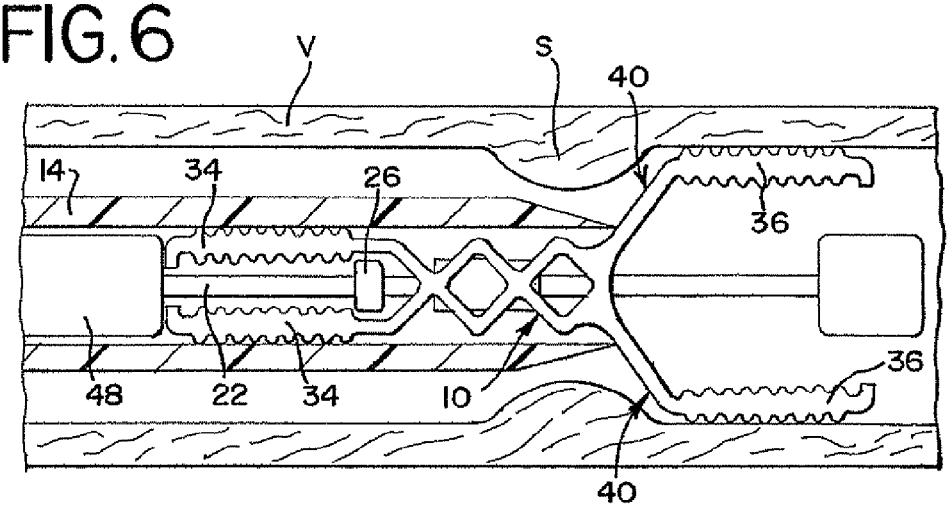
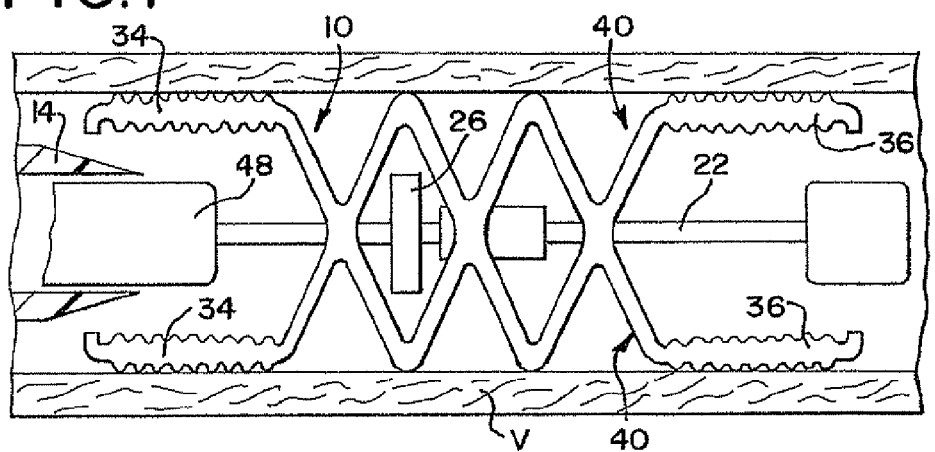

STENT DELIVERY SYSTEM WITH IMPROVED RETRACTION MEMBER

This is a divisional of and claims priority from U.S. patent application Ser. No. 11/380,819, filed Apr. 28, 2006, incorporated by reference hereinto.

FIELD OF THE INVENTION

The disclosed invention relates to intraluminal therapeutic devices and delivery systems therefor, and more particularly, to expandable stents and delivery systems which may be used in the treatment of body vessel defects. This invention also relates to the deployment and repositioning of expandable stents within body vessels, especially those within the brain.

DESCRIPTION OF RELATED ART

On a worldwide basis, nearly one million balloon angioplasties are performed annually to treat vascular diseases such as blood vessels that are clogged or narrowed by a lesion or stenosis. The objective of this procedure is to increase the inner diameter of the partially occluded blood vessel lumen. In an effort to prevent restenosis without requiring surgery, short flexible cylinders or scaffolds, referred to as stents, are often placed into the body vessel at the site of the stenosis or defect. Stents are typically made of metal or polymers and are widely used for reinforcing diseased body vessels. Stents are also useful in treating aneurysms by providing an internal lumen to cover an aneurysm and thus reduce the flow of blood and the pressure within the aneurysm, Some stents are expanded to their proper size using a balloon catheter. Such stents are referred to as "balloon expandable" stents. Other stents, referred to as "self-expanding" stents, are designed to elastically resist compression in a self-expanding manner. Balloon expandable stents and self-expanding stents are compressed into a small diameter cylindrical form and deployed within a body vessel using a catheter-based delivery system.

Stents have been developed with radiopaque markers to aid in the visualization of the stent upon deployment. Radiopaque markers facilitate the positioning of the stent within a body vessel by allowing a physician to determine the exact location, size, and orientation of the stent under x-ray or fluoroscopy. These markers are typically formed of a radiopaque material such as tantalum, zirconium, titanium, or platinum. Published U.S. Patent Application No. 2002/0082683 to Stinson at al., which is hereby incorporated herein by reference, discloses one such radiopaque marker comprised of a pigtail, knot, or ring, of tantalum wire wrapped around a crossing point of struts within a stent.

SUMMARY OF THE INVENTION

In accordance with one aspect of the present invention, an expandable stent and a stent delivery system are provided. The delivery system includes an elongated core member with a distal portion and a non-cylindrical retraction member disposed about the distal portion. The stent is a tubular member having a thin wall and an anchor member extending away from the thin wall. An extending portion of the retraction member is engageable with a distal portion of the anchor member when the stent is compressed onto the core member by a deployment catheter of the delivery system. A radius of the extending portion of the retraction member is greater than a compressed inner radius of the tubular member when the stent is compressed onto the core member.

In accordance with another aspect of the present invention, a method of deploying an expandable stent within a body vessel is provided. The method involves providing a self-expanding stent and delivery system. The stent is mounted about a distal portion of an elongated core member of the delivery system. The stent has a thin wall and an anchor member extending away from the thin wall. An extending portion of the retraction member is engageable with a distal portion of the anchor member when the stent is compressed onto the core member by a deployment catheter of the delivery system. A radius of the extending portion of the retraction member is greater than a compressed inner radius of the tubular member when the stent is compressed onto the core member. The stent and at least a portion of the delivery system are inserted into a body vessel, and then the stent is positioned adjacent to a defect of the body vessel. When the stent is properly positioned, the deployment catheter is moved proximally with respect to the core member, which allows the stent to begin expanding within the body vessel. Finally, the deployment catheter is moved further proximally with respect to the core member, which allows the stent to fully deploy.

In accordance with yet another aspect of the present invention, a method of resheathing an expandable stent within a body vessel is provided. The method involves providing a self-expanding stent and delivery system. The stent is mounted about a distal portion of an elongated core member of the delivery system. The stent has a thin wall and an anchor member extending away from the thin wall. An extending portion of the retraction member is engageable with a distal portion of the anchor member when the stent is compressed onto the core member by a deployment catheter of the delivery system. A radius of the extending portion of the retraction member is greater than a compressed inner radius of the tubular member when the stent is compressed onto the core member. The expandable stent and at least a portion of the delivery system are inserted into a body vessel, and then the stent is positioned adjacent to a defect of the body vessel. When the stent is properly positioned, the deployment catheter is moved proximally with respect to the core member, which allows the stent to begin expanding within the body vessel. If it is determined that the stent should be moved to a different position within the body vessel, then the deployment catheter is moved distally with respect to the core member, which forces the stent back into the cathether. When the stent is back in the cathether, the delivery system can be relocated.

Other aspects, objects and advantages of the present invention, including the various features used in various combinations, will be understood from the following description according to preferred embodiments of the present invention, taken in conjunction with the drawings in which certain specific features are shown.

BRIEF DESCRIPTION OF THE DRAWINGS

FIG. 1 is a partial sectional view of an expandable stent and a delivery system in accordance with an embodiment of the present invention;

FIG. 1A is a cross sectional view of the retraction member of FIG. 1, taken through the line 1A-1A of FIG. 1;

FIG. 1B is a plan view of an alternative retraction member profile;

FIG. 2 is a partial sectional view of an expandable stent and a delivery system in accordance with another embodiment of the present invention;

FIG. 3 is a cross sectional view of the stent and delivery system of FIG. 2, with anchor members having an outer layer;

FIG. 4A is an enlarged perspective view of an anchor member having an integral threaded portion, according to an aspect of the present invention;

FIG. 4B is an enlarged perspective view of an anchor member having an outer layer according to another aspect of the present invention;

FIG. 5 is a partial sectional view of the expandable stent and delivery system of FIG. 1 in a body vessel;

FIG. 6 is a partial sectional view of the delivery system with the deployment catheter moved proximally, allowing the distal section of the expandable stent to expand within the body vessel, while the proximal section of the expandable stent remains interlocked within the deployment catheter; and FIG. 7 is a partial sectional view of the delivery system with the deployment catheter moved proximally and the expandable stent fully expanded within the body vessel.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 illustrates an expandable stent 10 and delivery system 12. The delivery system 12 includes a deployment catheter or microcatheter (not shown in FIG. 1), which takes the form of an elongated tube having a lumen 16, and an introducer 13. A proximal section 18 of the deployment catheter 14 is sufficiently flexible to traverse a body vessel, typically a blood vessel, but is sufficiently rigid so that it can be pushed distally through the body vessel. A distal section 20 of the deployment catheter 14 is preferably formed of a material that is more flexible than the proximal section 18, for enhanced maneuverability through a tortuous stretch of a body vessel. For example, the proximal section 18 may be substantially comprised of stainless steel, while the distal section 20 may be substantially comprised of a nitinol material in a superelastic state at body temperature.

The delivery system 12 also includes an elongated core member 22 which is formed of wire, preferably nitinol, but may also be formed from other metal alloys or a polymer material. The core member 22 is axially movable within the lumen 16 of the deployment catheter 14 and can have a varying diameter, as will be described in greater detail herein.

A distal portion 24 of the core member 22 includes a non-cylindrical retraction member 26, as illustrated in FIGS. 1-3. The shape of the retraction member 26 depends on the configuration of the associated stent 10, but as illustrated in FIG. 1A, it includes at least one extending portion 28 that extends between adjacent struts 30 of the stent 10, thereby achieving a larger radius R than a compressed inner radius r of the stent 10 when the same is compressed onto the core member 22. In the embodiment of FIG. 1A, the retraction member 26 has a gear- or spur-shaped profile with a plurality of extending portions 28 arranged in a symmetrical configuration, which may be preferred to maintain the core member 22 centered within the deployment catheter 14. FIG. 1B shows an alternative retraction member 26a that uses a polygonal profile to provide a plurality of extending portions 28a. Other profiles are possible and the scope of the present invention is not limited to the particular geometries of the illustrated retraction members 26 and 26a.

The retraction member 26 may be integrally formed with the core member 22, but it typically is a separate piece, such as a collar or ring, that is rigidly affixed to the core member 22. The means for affixing the retraction member 26 to the core member 22 may vary according to a number of factors, such as the materials of the surfaces to be joined, but suitable means may include welding, spot welding, brazing, soldering, and thermal interference fitting. Rather than providing a single collar or ring, each extending portion 28 may be separately affixed to the core member 22, but such an operation typically is not preferred because it is labor intensive and may result in misaligned or staggered extending portions.

As for the self-expanding stent 10, it is removably mounted on the core member 22 for movement therewith through the deployment catheter 14. Examples of suitable core members are illustrated in FIGS. 1, 2, and 3. The expandable stent 10 may take on many different patterns or configurations, such as those disclosed in U.S. Pat. Nos. 6,673,106 and 6,818,013, both to Mitelberg et al. and both of which are hereby incorporated herein by reference. The stent 10 may be coated with an agent, such as heparin or rapamycin, to prevent stenosis or restenosis of the vessel. Examples of such coatings are disclosed in U.S. Pat. Nos. 5,288,711 to Mitchell et al.; U.S. Pat. No. 5,516,781 to Morris et al.; U.S. Pat. No. 5,563,146 to Morris et al.; and U.S. Pat. No. 5,646,160 to Morris et al., all of which are hereby incorporated herein by reference.

The illustrated stent 10 of FIGS. 1, 2, and 3 is laser cut from a tubular piece of nitinol to form a skeletal tubular member 32. The skeletal tubular member 32 has a thin wall, a small diameter, and when cut forms a plurality of cells which are created by a plurality of interconnected struts 30. The nitinol is preferably treated so as to exhibit superelastic properties at body temperature.

The stent 10 includes at least one anchor member 34, an example of which is illustrated in detail in FIG. 4A, extending away from the tubular member 32. Preferably, the stent 10 includes a plurality of anchor members 34 and 36 extending away from a proximal section 38 and a distal section 40, respectively, of the tubular member 32, as illustrated in FIGS. 1, 2, and 3. In one preferred embodiment, the stent 10 includes eight anchor members, with four extending from each of the proximal and distal sections 38 and 40 of the stent tubular member 32.

If anchor members 34, 36 are provided at both sides of the stent 10, then a second retraction member 42 can be provided for engagement with the distal anchor members 36. Each retraction member preferably has a plurality of separate extending members 28, each one adapted for engagement with one or more of the anchor members. Typically, a one-to-one engagement is preferred. For example, FIG. 1A shows a stent 10 with four proximal anchor members 34, each of which is engageable by a separate extending member 28 of the proximal retraction member 26.

The illustrated anchor members 34, 36 include a threaded portion 44, as described generally in U.S. Pat. No. 6,955,685 to Escamilla et al., which is hereby incorporated herein by reference. An anchor member with an integral threaded portion 44 is illustrated in FIG. 4A. Depending on the material used to form the stent 10, there are a number of different ways to form the threaded portion 44. For example, the threaded portion 44 may be formed by cutting threads into the anchor member 34, 36 when the stent 10 is laser cut from a nitinol tubular member. Alternatively, a heat-molding technique may be used to form the threaded portion 44 on the anchor member 34, 36. Those of ordinary skill in the art will appreciate that the present invention may be practiced regardless of the method of forming the threaded portion 44, if one is provided.

Additionally, as illustrated in FIGS. 3 and 4B, an outer layer 46 may be deposited or wound about at least a portion of the anchor member 34,36 or threaded portion 44 in order to increase its diameter or to provide other performance characteristics. For example, in a preferred embodiment, the threaded portion 44 is wound with a radiopaque material defining a marker coil. The marker coil may be formed of a metallic or polymeric material that exhibits the characteristic of being radiopaque, such as tantalum or tantalum alloy. The marker coil may also be comprised of gold, gold alloy, platinum, platinum alloy, titanium, zirconium, bromine, iodine, barium, bismuth, or any combination thereof. In addition to increasing the diameter of the anchor member 34,36, an outer layer provided as a marker coil serves as a radiopaque marker for improved visualization during the deployment of the stent within a body vessel.

In the case where an outer layer is applied to the anchor member 34,36, the outer layer is preferably secured to the anchor member 34,36 using an adhesive material, such as a UV adhesive which is thermally cured.

Regardless of the geometry of the anchor member 34,36 and whether it includes an outer layer 46, it preferably is thicker than the thin wall of the stent 10, as illustrated in FIGS. 1A and 2. The proximal anchor members 34 interacts with the proximal retraction member 26 in order to retract a partially deployed stent, as will be described herein, so it should be reinforced for improved retractability.

As illustrated in FIGS. 1, 2 and 3, the stent 10 is delivered to a body vessel by the delivery catheter 14. The stent 10 and associated core member 22 are axially movable together within the delivery catheter 14. The stent 10 is preferably removably locked onto the core member 22 by axially trapping the proximal anchor members 34 between the extending portions 28 of the proximal retraction member 26 and a cylindrical member 48 disposed about the distal portion 24 of the core member 22. The general configuration and function of such a cylinder may be seen in U.S. Pat. No. 6,833,003 to Jones at al., which is hereby incorporated herein by reference.

As illustrated in FIGS. 1, 2, and 3, the cylindrical member 48 may be spaced from the extending portions 28 of the retraction member 26 to define a gap that receives the anchor members 34. Preferably, the length of the anchor members 34 is substantially equal to the length of the gap in order to prevent the anchor members 34, and hence the stent 10, from shifting position along the core member 22. In the embodiment of FIGS. 2 and 3, a second retraction member 42 and a second cylindrical member 50 are provided distally of the first retraction member 26 in order to define a second gap for securing the distal anchor members 36. If only one retraction member 26 is provided, then it is preferably located proximally of the stent tubular member 32 to interlock with the proximal anchor members 34. This is useful for retracting and repositioning the stent 10, as will be described herein.

In a preferred embodiment, an intermediate cylindrical member 52 is provided on which to mount the stent 10. FIG. 1 shows the proximal retraction member 26 spaced from the intermediate cylinder 52, while FIGS. 2 and 3 show the retraction member 26 extending from the intermediate cylinder 52. If the core member 22 is provided with an intermediate cylindrical member 52, but without a distal retraction member, then any distal anchor members 36 may be trapped in a gap defined between the intermediate cylindrical member 52 and the distal cylindrical member 50. It is preferred to have at least some means for removably locking the distal anchor members 36 to the core member 22 in order to discourage the stent distal section 40 from clinging to the delivery catheter 14 and "bunching up" during deployment of the stent 10.

FIG. 5 illustrates the self-expanding stent 10 and delivery system 12 of FIG. 1 positioned within a body vessel V. Initially, the stent 10 is interlocked to the core member 22 by positioning the proximal anchor members 34 within the gap defined between the proximal cylinder 48 and the retraction member 26. If a core member means for receiving the distal anchor members 36 is provided, then the distal anchor members 36 may be similarly secured. The core member 22 is then slid into the deployment catheter 14 to thereby compress the thin wall of the stent 10 into a compressed condition against the core member 22. When the stent 10 is positioned within the delivery catheter 14, the delivery system 12 is inserted into the body vessel V and advanced distally until the stent 10 is aligned with a vessel defect S. Although the delivery system 12 is illustrated in use with a stenosed body vessel, it will be appreciated that it may be used with any other vessel defect treatable with a stent, such as an aneurysm.

FIG. 6 shows the deployment catheter 14 moved proximally, releasing the distal anchor members 36 and allowing the distal section 40 of the expandable stent 10 to begin expanding. During expansion, the distal section 40 of the stent 10 comes in contact with the wall of the body vessel V.

As illustrated in FIG. 7, the deployment catheter 14 is again moved proximally, releasing the proximal anchor members 34 and allowing the stent 10 to fully expand. Once the stent 10 is fully deployed within the body vessel V, the core member 22 remains extended through the stent 10 and thus acts as a guide wire, providing a physician with easier access to locations within the body vessel distal of the stent 10.

If, during the deployment process, it is determined that the stent 10 should be relocated or realigned, the deployment catheter 14 may be used to resheath the stent 10. With the stent 10 positioned on the core member 22 as described above with reference to FIG. 6, the proximal anchor members 34 will remain interlocked in the gap between the proximal cylindrical member 48 and the proximal retraction member 26. In this configuration, the stent 10 may be resheathed. To resheath the stent 10, the deployment catheter 14 is moved distally, thereby forcing the stent 10 back into the catheter 14 and onto the core member 22, compressing the distal section 40 of the stent 10, and forcing the distal anchor members 36 into engagement with the core member 22. The stent 10 and delivery system 12 may then be withdrawn or repositioned to a different location within the body vessel V.

It will be appreciated that, during the retraction step, a distal portion 54 of the proximal anchor members 34, best illustrated in FIG. 1A, will contact the extending portions 28 of the proximal retraction member 26. The extending portions 28 pass between adjacent struts 30 of the stent 10, thereby allowing the radii R of the extending portions 28 of the retraction member 26 to exceed a compressed inner radius r of the stent wall or tubular member 32. In contrast, a cylindrical retraction member, similar to the intermediate cylinder 52 described previously, has a definite size limitation because the cylinder is necessarily bounded by the inner surface of the stent. Thus, it will be appreciated that the provision of a retraction member 26 that is non-cylindrical in transverse cross-section or end profile (examples being shown in FIG. 1A and FIG. 1B) allows for a greater contact area with a distal portion 54 of the proximal anchor members 34, which increased contact area improves the retractability of the stent 10.

When the expandable stent 10 has been properly positioned and fully expanded within the blood vessel V, as illustrated in FIG. 7, the delivery catheter 14 and the core member 22 are removed from the body.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An expandable stent and stent delivery system comprising:
 a delivery system including an elongated core member having a distal portion and a retraction member disposed about the distal portion of said elongated core member;
 said retraction member has a non-cylindrical transverse cross-sectional profile and at least one extending portion of the retraction member;
 a self-expanding stent comprising a small diameter tubular member having a thin wall, at lest one anchor member extending away from said thin wall, said extending portion of the retraction member being engageable with a distal portion of said anchor member when the stent is compressed onto said core member;
 a deployment catheter having a lumen extending therethrough and adapted for coaxial placement about said elongated core member such that said deployment catheter compresses the stent tubular member onto said distal portion of the core member in a compressed condition having a compressed inner radius; and
 said extending portion of the retraction member has a radius greater than said compressed inner radius of the stent tubular member.

2. The expandable stent and stent delivery system of claim 1, wherein said anchor member has a thickness greater than a thickness of said stent tubular member.

3. The expandable stent and stent delivery system of claim 1, wherein said anchor member extends away from a proximal section of the expandable stent.

4. The expandable stent and stent delivery system of claim 3, wherein a further extending portion of the retraction member has a radius greater than said compressed inner radius of the stent tubular member, and a further anchor member extends away from said proximal section of the expandable stent, wherein said further extending portion of the retraction member is engageable with a distal portion of said further anchor member when the stent is compressed onto said core member.

5. The expandable stent and stent delivery system of claim 1, wherein said retraction member has a substantially spur-shaped profile.

6. The expandable stent and stent delivery system of claim 1, wherein said retraction member has a substantially polygonal profile.

7. The expandable stent and stent delivery system of claim 1, further comprising a cylindrical member disposed about the distal portion of said elongate core member.

8. The expandable stent and stent delivery system of claim 7, wherein said cylindrical member is spaced from said extending portion of the retraction member to define a gap, and wherein said gap receives said anchor member.

* * * * *